US012778528B2

(12) United States Patent
Yoshida et al.

(10) Patent No.: US 12,778,528 B2
(45) Date of Patent: Nov. 3, 2026

(54) MEDICAL INFORMATION PROCESSING DEVICE, MEDICAL INFORMATION PROCESSING METHOD, AND STORAGE MEDIUM

(71) Applicants: OSAKA UNIVERSITY, Suita (JP); Canon Kabushiki Kaisha, Tokyo (JP)

(72) Inventors: Takeshi Yoshida, Suita (JP); Yuji Fujino, Suita (JP); Kota Aoyagi, Nasushiobara (JP)

(73) Assignees: OSAKA UNIVERSITY, Suita (JP); Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/916,815

(22) Filed: Oct. 16, 2024

(65) Prior Publication Data

US 2025/0281134 A1 Sep. 11, 2025

(30) Foreign Application Priority Data

Oct. 18, 2023 (JP) ................................ 2023-179486

(51) Int. Cl.

| | |
|---|---|
| ***A61B 8/00*** | (2006.01) |
| ***A61B 5/03*** | (2006.01) |
| ***A61B 5/085*** | (2006.01) |
| ***A61B 6/03*** | (2006.01) |
| ***A61B 6/46*** | (2024.01) |

(52) U.S. Cl.
CPC .............. *A61B 6/463* (2013.01); *A61B 5/037* (2013.01); *A61B 5/085* (2013.01); *A61B 6/032* (2013.01)

(58) Field of Classification Search
CPC ........... A61B 5/037; A61B 5/08; A61B 5/085; A61B 6/032; A61B 6/463; A61B 6/5217
See application file for complete search history.

(56) References Cited

U.S. PATENT DOCUMENTS

2021/0233241 A1* 7/2021 Washko, Jr. ........... G16H 30/40
2022/0130040 A1* 4/2022 Peterson .................. G06T 7/62
2022/0142559 A1 5/2022 Kawada

FOREIGN PATENT DOCUMENTS

JP 2020-178936 A 11/2020

* cited by examiner

*Primary Examiner* — Mark D Remaly
(74) *Attorney, Agent, or Firm* — Oblon, McClelland, Maier & Neustadt, L.L.P.

(57) ABSTRACT

A medical information processing device of an embodiment includes processing circuitry. The processing circuitry is configured to acquire a CT image of a chest of a subject, acquire an esophageal pressure and an airway pressure of the subject, generate a risk information map in a lung field of the subject on a basis of the CT image, the esophageal pressure, and the airway pressure, estimate risk information in the lung field of the subject on a basis of the risk information map, and display the risk information map and the risk information on a display.

9 Claims, 8 Drawing Sheets

MEDICAL INFORMATION PROCESSING DEVICE, MEDICAL INFORMATION PROCESSING METHOD, AND STORAGE MEDIUM

CROSS-REFERENCE TO RELATED APPLICATION

The present application claims priority based on Japanese Patent Application No. 2023-179486 filed Oct. 18, 2023, the content of which is incorporated herein by reference.

FIELD

Embodiments disclosed in the present specification and drawings relate to a medical information processing device, a medical information processing method, and a storage medium.

BACKGROUND

In the artificial respiration management of patients with acute respiratory distress syndrome (ARDS), a lung protective ventilation strategy based on limiting the tidal volume is recommended to prevent ventilator-associated lung injury due to alveolar hyperextension. Transpulmonary pressure, which is a determining factor of ventilator-associated lung injury, is measured by a transpulmonary pressure measurement method using an esophageal balloon or the like.

In the lung protective ventilation strategy in the related art, a uniform artificial respiration management is performed for all patients with the same tidal volume (6 ml/kg). As a result, the mortality rate of patients remains extremely high. For this reason, a method is required to establish an individualized lung protective ventilation strategy for each patient according to the degree of risk of ventilator-associated lung injury. In order to establish an individualized lung protective ventilation strategy, it is necessary to accurately ascertain the transpulmonary pressure, which is a determining factor of ventilator-associated lung injury that differs from patient to patient. However, transpulmonary pressure measurement methods using an esophageal balloon or the like in the related art reflect the transpulmonary pressure in a specific local lung region and are unable to ascertain the accurate transpulmonary pressure in the entire lung. As a result, it is not possible to appropriately evaluate the risk of ventilator-associated lung injury.

DETAILED DESCRIPTION

A medical information processing device, a medical information processing method, and a storage medium of an embodiment will be described below with reference to the drawings. The medical information processing device of the embodiment generates a risk information map showing a lung injury risk in the lung field of a patient on the basis of a CT image, esophageal pressure, and airway pressure of the subject (patient), estimates risk information in the lung field of the patient, and displays the risk information map and the risk information on a display, thereby enabling a detailed and accurate evaluation of the risk of lung injury.

A medical information processing device of an embodiment includes processing circuitry. The processing circuitry is configured to acquire a CT image of a chest of a subject, acquire an esophageal pressure and an airway pressure of the subject, generate a risk information map in a lung field of the subject on a basis of the CT image, the esophageal pressure, and the airway pressure, estimate risk information in the lung field of the subject on a basis of the risk information map, and display the risk information map and the risk information on a display.

<Configuration of Medical Information Processing Device 100>

Figure 1:
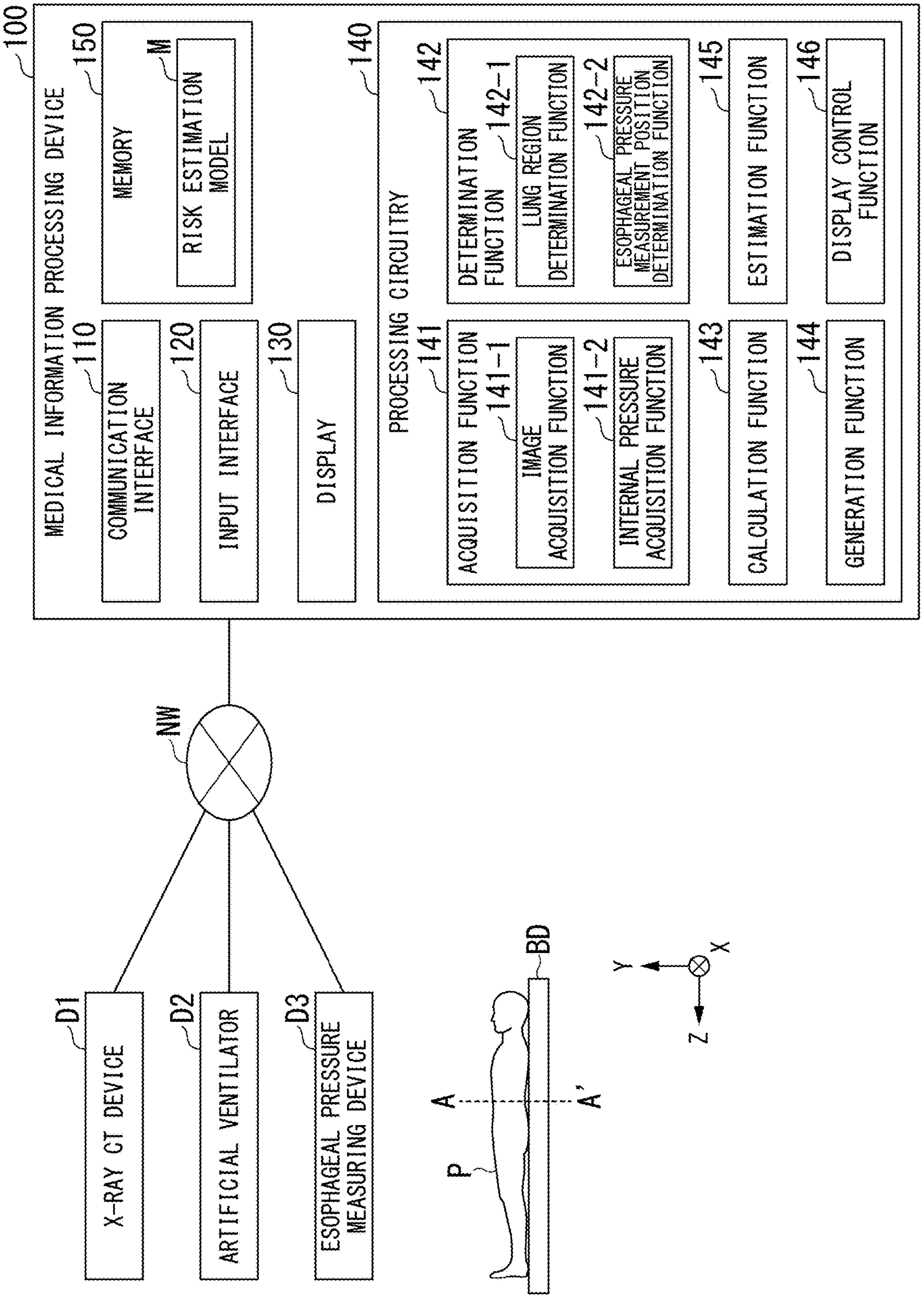
FIG. 1 is a functional block diagram showing an example of a medical information processing device 100 according to an embodiment.

FIG. 1 is a functional block diagram showing an example of a medical information processing device 100 according to an embodiment. For example, the medical information processing device 100 is operated by a user such as a doctor or a technician who examines and treats patients. The medical information processing device 100 is, for example, a computer apparatus (a terminal device such as a personal computer or a tablet) used in a CT examination room, an operating room, a hospital room, and the like. The medical information processing device 100 is connected to external devices (medical apparatuses, modalities, and the like) such as an X-ray CT device D1, an artificial ventilator D2, and an esophageal pressure measuring device D3 via a communication network NW such that they can communicate with each other. The medical information processing device 100 may be a server device that is connected to terminal devices used by doctors and others via a network.

The medical information processing device 100 includes, for example, a communication interface 110, an input interface 120, a display 130, processing circuitry 140, and a memory 150. The communication interface 110 communicates with an external device via a communication network NW. The communication network NW may refer to a general information and communication network that uses electrical communication technology. For example, the communication network NW includes telephone communication line networks, optical fiber communication networks, cable communication networks, and satellite communication networks in addition to wireless/wired LANs such as a hospital backbone local area network (LAN) and the Internet. The communication interface 110 includes, for example, a network interface card (NIC) and an antenna for wireless communication.

The input interface 120 receives various input operations from a user (operator), converts the received input operations into electrical signals, and outputs the electrical signals to the processing circuitry 140. For example, the input interface 120 includes a mouse, a keyboard, a trackball, a switch, a button, a joystick, a touch panel, and the like. The input interface 120 may be, for example, a user interface that receives voice input, such as a microphone. If the input interface 120 is a touch panel, the input interface 120 may also have the display function of the display 130.

Note that in this specification, the input interface 120 is not limited to an interface that has physical operating parts such as a mouse and a keyboard. For example, examples of the input interface 120 also include electrical signal processing circuitry that receives an electrical signal corresponding to an input operation from an external input apparatus provided separately from the device and outputs the electrical signal to control circuitry.

The display 130 provides various types of information to a user. The display 130 displays, for example, CT images and various measurement values acquired from external devices, a risk information map generated by the processing circuitry 140, a graphical user interface (GUI) image for receiving various input operations from a user, and the like. The display 130 is, for example, a liquid crystal display or the like. The display 130 may be provided separately from the medical information processing device 100. The display 130 is an example of a "display."

The processing circuitry 140 controls the overall operation of the medical information processing device 100. The processing circuitry 140 includes, for example, an acquisition function 141, a determination function 142, a calculation function 143, a generation function 144, an estimation function 145, and a display control function 146. The processing circuitry 140 realizes these functions, for example, by a hardware processor executing a program stored in a storage device (storage circuitry).

The hardware processor refers to circuitry such as a central processing unit (CPU), a graphics processing unit (GPU), an application specific integrated circuit (ASIC), a programmable logic device (e.g., simple programmable logic device (SPLD) or complex programmable logic device (CPLD)), or a field programmable gate array (FPGA). Instead of being stored in the storage device, the program may be directly built into the circuit of the hardware processor. In this case, the hardware processor realizes the functions by reading and executing the program built into the circuit. The hardware processor is not limited to being configured as a single circuit and may be configured as a single hardware processor by combining a plurality of independent circuits to realize each function. The storage device may be a non-transitory (hardware) storage medium. Further, a plurality of components may be integrated into a single hardware processor to realize each function.

The acquisition function 141 acquires various types of medical information from external devices via the communication network NW. The acquisition function 141 includes, for example, an image acquisition function 141-1 and an internal pressure acquisition function 141-2.

The image acquisition function 141-1 acquires CT images of the chest of a patient P from the X-ray CT device D1. The CT images include, for example, a plurality of tomographic images of the patient P sliced in the XY plane (A-A' cross section in FIG. 1) in the range of the chest (for example, at least two-thirds of the lower thoracic esophagus) in the body axis direction (Z direction) of the patient P placed on a bed device BD of the X-ray CT device D1. The body axis direction of the patient P is defined as the Z axis direction (the longitudinal direction of the tabletop of the bed device BD), the axis orthogonal to the Z axis direction and horizontal to the floor surface is defined as the X axis direction, and the direction orthogonal to the Z axis direction and perpendicular to the floor surface is defined as the Y axis direction. The image acquisition function 141-1 may acquire a CT image from a database (for example, a picture archiving and communication system (PACS)) in which captured CT images are stored. The image acquisition function 141-1 may acquire a single CT image of the patient P from the X-ray CT device D1. The image acquisition function 141-1 is an example of an "image acquirer."

The internal pressure acquisition function 141-2 acquires information indicating the airway pressure and esophageal pressure of the patient P. The airway pressure information is acquired, for example, from the artificial ventilator D2 connected to the lungs via the mouth, throat, and the like of the patient P. The esophageal pressure information is acquired, for example, from the esophageal pressure measuring device D3. For example, an esophageal pressure tube or an esophageal pressure balloon kit for measuring an esophageal pressure is used as the esophageal pressure measuring device D3. For example, before or after CT imaging, an esophageal pressure balloon kit is placed in the esophagus of the patient P through the mouth or the like of the patient P. Thereafter, the esophageal balloon placed in the esophagus of the patient P is filled with an appropriate amount of air, the presence of a cardiac waveform and the appropriate placement position of the esophageal balloon are checked using the Baydur occlusion method or the like, and then the esophageal pressure is measured. The esophageal pressure measured in this manner is used as a substitute for the pleural pressure. The internal pressure acquisition function 141-2 is an example of an "internal pressure acquirer."

The determination function 142 performs image analysis on an acquired CT image to determine the characteristics of the chest on the CT image. For example, any method such as segmentation using machine learning technology can be used as the image analysis. The determination function 142 includes, for example, a lung region determination function 142-1 and an esophageal pressure measurement position determination function 142-2. The lung region determination function 142-1 determines a lung region indicating a region in which lungs are imaged in a CT image. The esophageal pressure measurement position determination function 142-2 determines an esophageal pressure measurement position indicating a position where an esophageal balloon is placed in the esophagus and the esophageal pressure is measured in a CT image. The determination function 142 may determine or correct a lung region and an esophageal pressure measurement position on the basis of information manually input by a user via the input interface 120. In particular, ARDS patients often have bilateral infiltrative shadows in the dorsal part. Depending on the method of automatically determining a lung region, an infiltrative shadow may not be correctly recognized as being within a lung region. Therefore, the user can perform manual correction via the input interface 120.

The calculation function 143 calculates a transpulmonary pressure for each unit region included in a region determined to be a lung region in a CT image. The calculation function 143 calculates the transpulmonary pressure for each unit region on the basis of a relative positional relationship of a unit region for which the transpulmonary pressure is to be calculated with respect to an esophageal pressure measurement position, a CT value of the unit region in the CT image, and actual measured values of the airway pressure and esophageal pressure. The unit region may correspond to each pixel in the CT image, or may be composed of a plurality of pixels. Details of processing of the calculation function 143 will be described later. The calculation function 143 is an example of a "calculator." The calculation function 143 calculates the proportion of unit regions having transpulmonary pressures equal to or greater than a threshold value on the basis of the transpulmonary pressure for each unit region.

The generation function 144 generates a risk information map (transpulmonary pressure map, Lang stress map) showing a transpulmonary pressure for each unit region on the basis of a calculated transpulmonary pressure value for each unit region. The risk information map divides the lung region of the patient P into small regions (unit regions) and visualizes the amount, location, and pattern of risk regions for lung injury on the basis of transpulmonary pressure values. Details of processing of the generation function 144 will be described later. The generation function 144 is an example of a "generator." That is, the generation function 144 generates a risk information map for the lung field of a subject on the basis of a CT image, an esophageal pressure, and an airway pressure.

The estimation function 145 estimates risk information for the lung region of the patient P on the basis of the risk information map. The risk information includes, for example, information indicating a high-risk region where the risk of lung injury is particularly high. The estimation function 145 estimates the risk information using, for example, a machine learning function using artificial intelligence (AI). The estimation function 145 may be realized by, for example, a deep neural network. Alternatively, the estimation function 145 may be implemented using other machine learning models such as a support vector machine, a decision tree, a random forest, and a logistic regression instead of a neural network. Details of processing of the estimation function 145 will be described later. The estimation function 145 is an example of an "estimator." The estimation function 145 estimates risk information using a risk estimation model that has been trained to output information indicating risk information when information based on a risk information map or a combination of information based on a risk information map and subject information is input.

The display control function 146 displays, on the display 130, a CT image and various measurement values acquired from external devices, a risk information map generated by the processing circuitry 140, risk information, a GUI image for receiving various input operations from the user, and the like. The display control function 146 is an example of a "display controller." The display control function 146 superimposes the risk information map on the CT image and displays the same on the display. The display control function 146 displays the proportion of unit regions having transpulmonary pressures equal to or greater than a threshold value on the display.

The memory 150 is realized, for example, by a semiconductor memory element such as a random access memory (RAM) or a flash memory, a hard disk, an optical disc, and the like. The memory 150 stores, for example, a risk estimation model M used in estimation processing in the estimation function 145. In addition, the memory 150 stores a CT image and various measurement values acquired from external devices, a risk information map generated by the processing circuitry 140, and the like. Such data may be stored in an external memory with which the medical information processing device 100 can communicate, instead of (or in addition to) the memory 150. The external memory is controlled by a cloud server that manages the external memory, for example, by the cloud server receiving a read/write request.

<Processing Flow>

Figure 2:
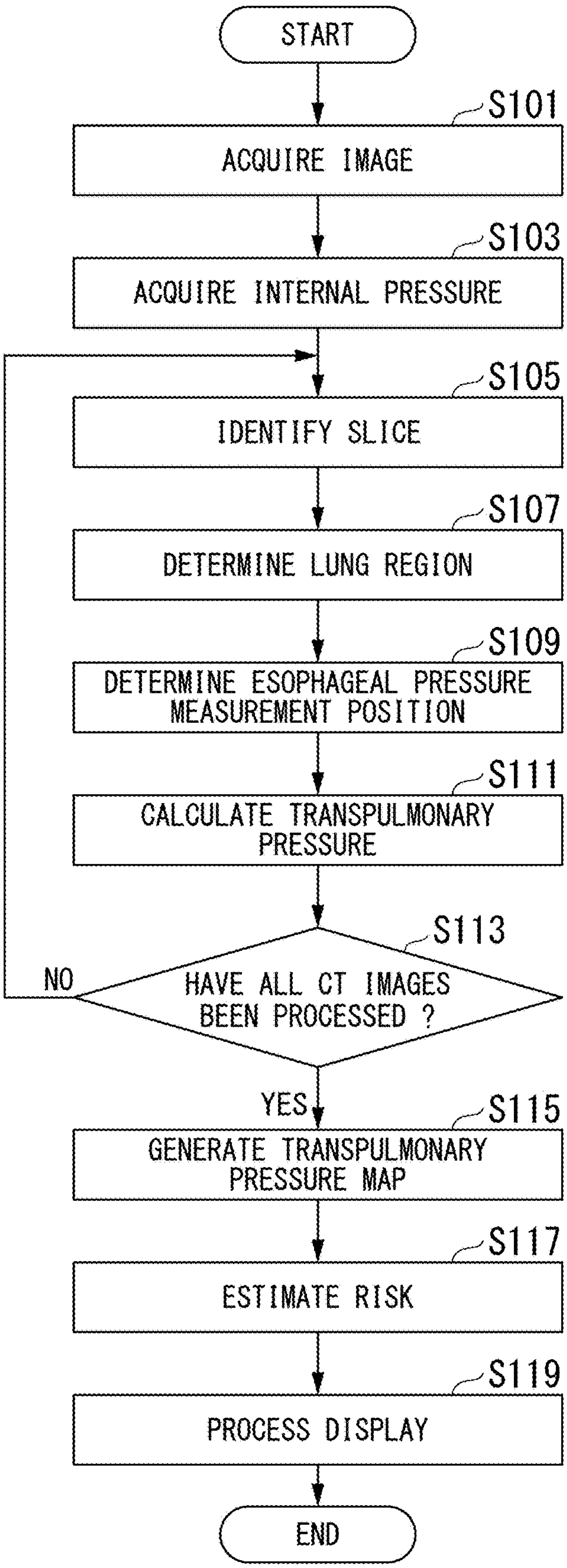
FIG. 2 is a flowchart showing an example of processing of the medical information processing device 100 according to an embodiment.

Next, a flow of processing performed by the medical information processing device 100 will be described. FIG. 2 is a flowchart showing an example of processing performed by the medical information processing device 100 according to an embodiment. In the following, it is assumed that processing is started with the patient P placed on the bed device BD of the X-ray CT device D1. The processing of the flowchart shown in FIG. 2 is started, for example, when a user issues an instruction to start risk evaluation processing via the input interface 120.

First, the image acquisition function 141-1 acquires CT images of the patient P from the X-ray CT device D1 (step S101). The CT images include, for example, a plurality of tomographic images of the patient P sliced in the XY plane in the range of the chest in the body axis direction (Z direction) of the patient P placed on the bed device BD.

Next, the internal pressure acquisition function 141-2 acquires information indicating the airway pressure and esophageal pressure of the patient P (step S103). The airway pressure information is acquired from the artificial ventilator D2. The esophageal pressure information is acquired from the esophageal pressure measuring device D3 using an esophageal balloon, for example. Note that the airway pressure measured with the same ventilator settings as those used during CT imaging may be acquired with respect to the inspiratory pressure and positive end-expiratory pressure (PEEP).

Next, the determination function 142 identifies one CT image of the slice position to be subjected to subsequent processing from among the acquired CT images (step S105). Next, the lung region determination function 142-1 performs image analysis on the extracted CT image to determine a lung region (step S107). Furthermore, the esophageal pressure measurement position determination function 142-2 performs image analysis on the extracted CT image to determine an esophageal pressure measurement position (step S109).

Figure 3:
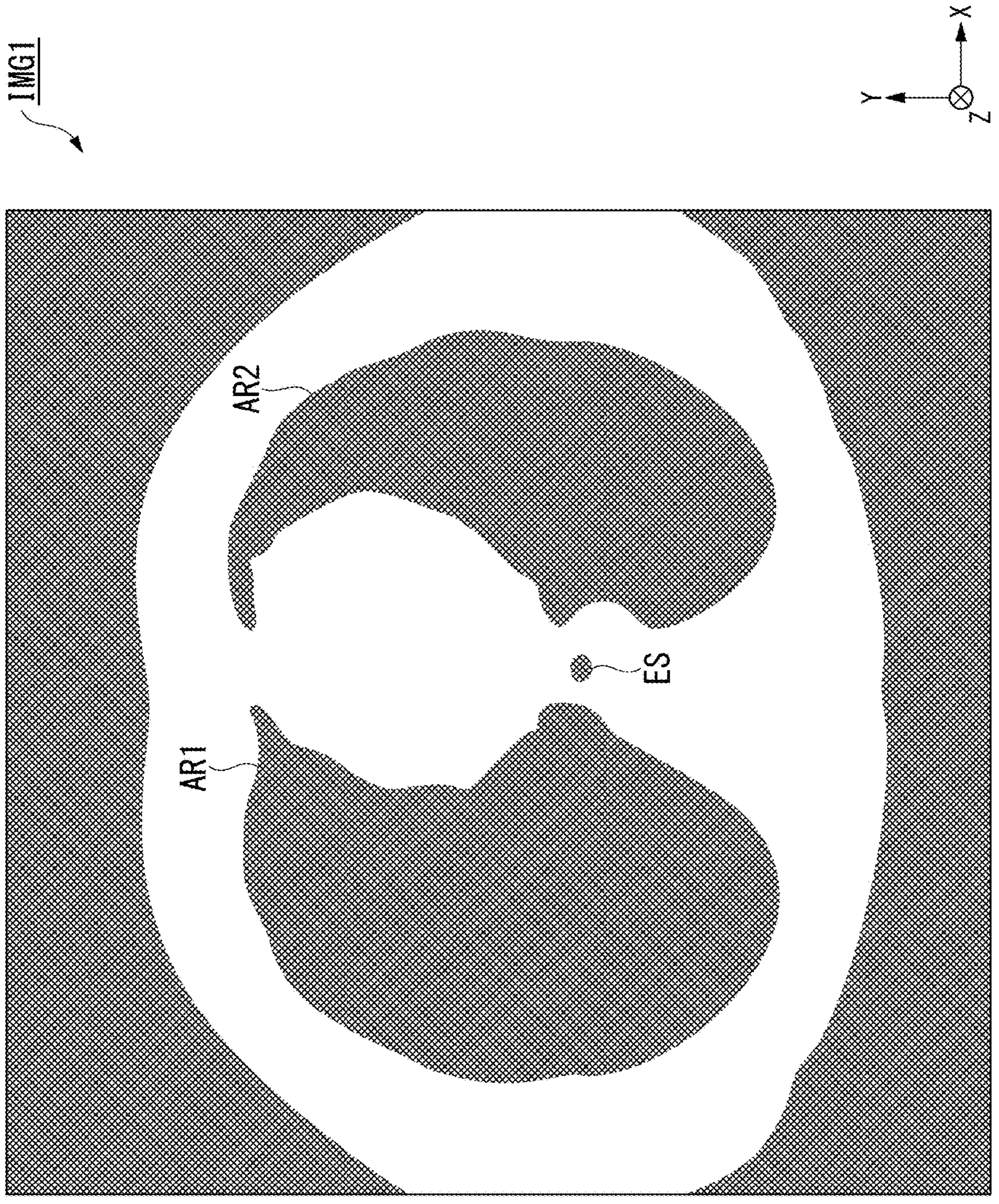
FIG. 3 is a diagram showing how a lung region and an esophageal pressure measurement position are determined in a CT image IMG1 according to an embodiment.

FIG. 3 is a diagram showing how a lung region and an esophageal pressure measurement position are determined in a CT image IMG1 according to an embodiment. In the example of FIG. 3, a lung region AR1 corresponding to the right lung and a lung region AR2 corresponding to the left lung are determined as lung regions, and further, an esophageal pressure measurement position ES indicating the position of the esophagus is determined as an esophageal pressure measurement position. If the slice position of the extracted CT image corresponds to the placement position of the esophageal balloon, the esophageal balloon will be located at the esophageal pressure measurement position ES.

Referring back to FIG. 2, subsequently, the calculation function 143 calculates a transpulmonary pressure (also called a "local transpulmonary pressure") for each unit region in the regions determined to be lung regions in the extracted CT image (step S111). The calculation function 143 calculates the transpulmonary pressure for each unit region on the basis of a relative position of the unit region with respect to the esophageal pressure measurement position ES, a CT value of the unit region, and actual measured values of the airway pressure and esophageal pressure.

Figure 4:
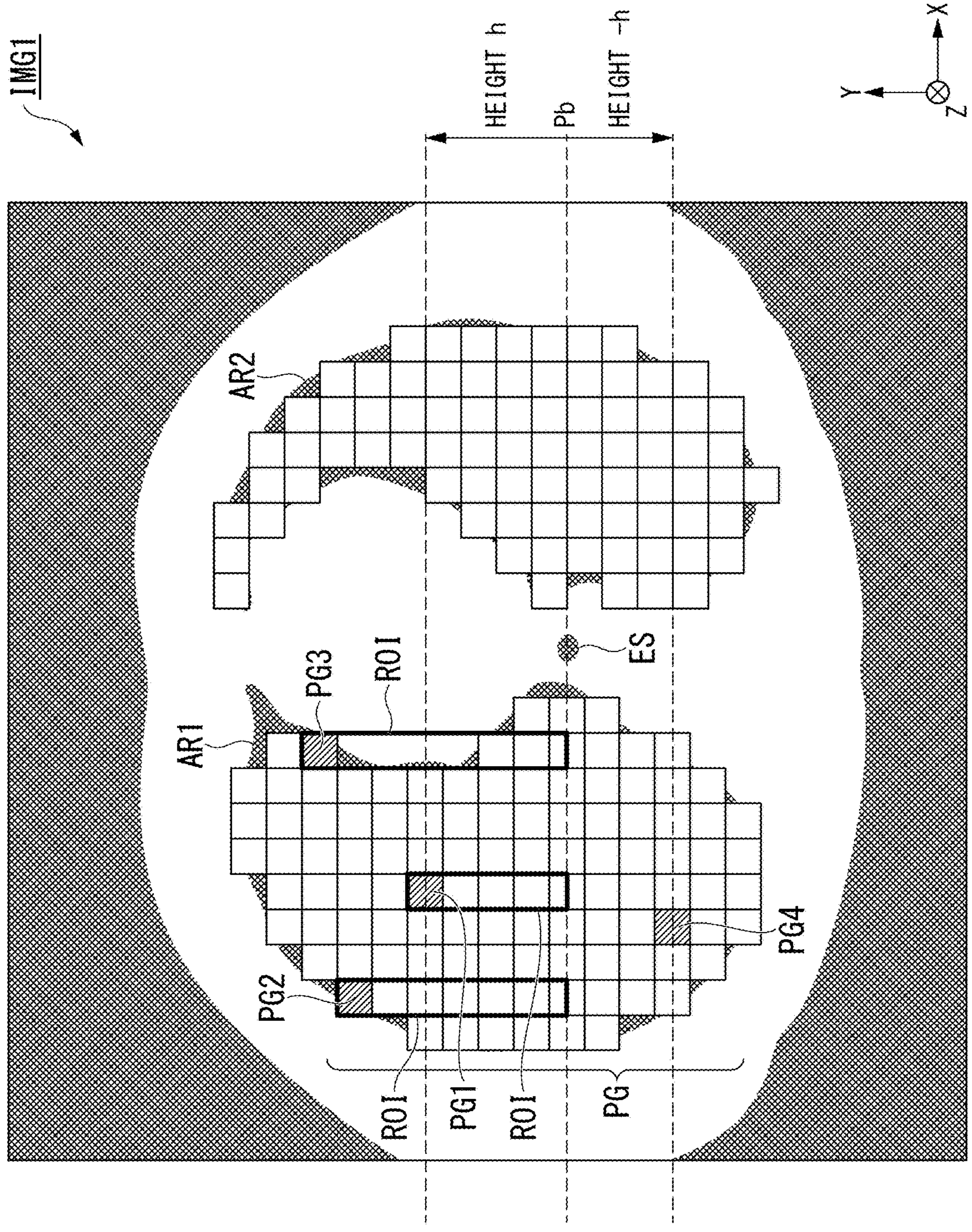
FIG. 4 is a diagram showing how a transpulmonary pressure for each unit region is calculated in the CT image IMG1 according to the embodiment.

FIG. 4 is a diagram showing how a transpulmonary pressure for each unit region is calculated in the CT image IMG1 according to an embodiment. As shown in FIG. 4, small regions (unit regions PG) having a predetermined area are set on the lung region AR1 and the lung region AR2. The unit region PG may correspond to one pixel of the CT image, or may be composed of a plurality of pixels. Here, for example, a case in which the position in the Y axis direction of the esophageal pressure measurement position ES is set as a height reference position Pb (height 0), and a transpulmonary pressure (local transpulmonary pressure) is calculated for a unit region PG1 corresponding to a position h [cm] higher in the Y-axis direction than the height reference position Pb will be described. If the average CT value of the part corresponding to the height h with respect to the unit region PG1 is $H_{Avg}$, the airway pressure acquired in step S103 is $P_{Airway}$ [$cmH_2O$], and the esophageal pressure acquired in step S103 is $P_{Esophagus}$ [$cmH_2O$], the local transpulmonary pressure $P_{Transpulmonary}$ [$cmH_2O$] in the unit region PG1 is calculated by the following formula (1).

$$P_{Transpulmonary} = P_{Airway} - \left[P_{Esophagus} - h*\{1-(H_{Avg}/-1000)\}\right] \quad \text{Formula (1)}$$

The average CT value $H_{Avg}$ of the part corresponding to height h is obtained by setting a rectangular region of interest ROI vertically downward from the unit region PG1, which is the calculation point of the local transpulmonary pressure, to the height reference position Pb, which is the height of the measurement position of the esophageal pressure, and averaging CT values of all pixels present in the region of interest ROI. Since a CT value is also a value indicating the density of a target region, information on the CT value can be used to calculate a transpulmonary pressure. The width of the region of interest ROI can be one pixel, or the region of interest ROI can have a width of a plurality of pixels having the unit region PG1 as a center. This can reduce noise caused by local deviations (errors) in CT values.

When the calculation point of the local transpulmonary pressure is near the edge of the lung, as in the unit regions PG2 and PG3, pixels outside the lung regions may be included in the region of interest ROI for calculating the average CT value. In this case, the average CT value $H_{Avg}$ may be obtained for pixels within the region of interest ROI and within the lung regions.

Further, when the calculation point of the local transpulmonary pressure is lower than the height reference position Pb, which is the measurement position of the esophageal pressure, as in the unit region PG4, the value of h in the above formula (1) is calculated as a negative value.

By repeating calculation of the local transpulmonary pressure with each unit region PG (each pixel or pixel group) within the lung regions as the calculation point of the local transpulmonary pressure, the numerical value of the transpulmonary pressure can be calculated for the entire lung region.

Referring back to FIG. 2, the processing circuitry 140 determines whether calculation processing of transpulmonary pressures has been completed for all acquired CT images (step S113). If it is determined that calculation processing of transpulmonary pressures has not been completed for all CT images (step S113; NO), processing returns to step S105 and the same processing is performed on unprocessed CT images.

On the other hand, if it is determined that calculation processing of transpulmonary pressures for all CT images has been completed (step S113; YES), the generation function 144 generates a transpulmonary pressure map (risk information map) on the basis of the transpulmonary pressure value for each unit region PG calculated for each CT image (step S115). Here, since a transpulmonary pressure map with respect to a plurality of tomographic images (CT images) in the range of the chest in the body axis direction of the patient P is obtained, a three-dimensional 3D transpulmonary pressure map is generated as a result. That is, the generation function 144 generates a three-dimensional risk information map in the body axis direction of the subject on the basis of CT images including a plurality of tomographic images of the chest captured in the body axis direction of the subject.

Figure 5:
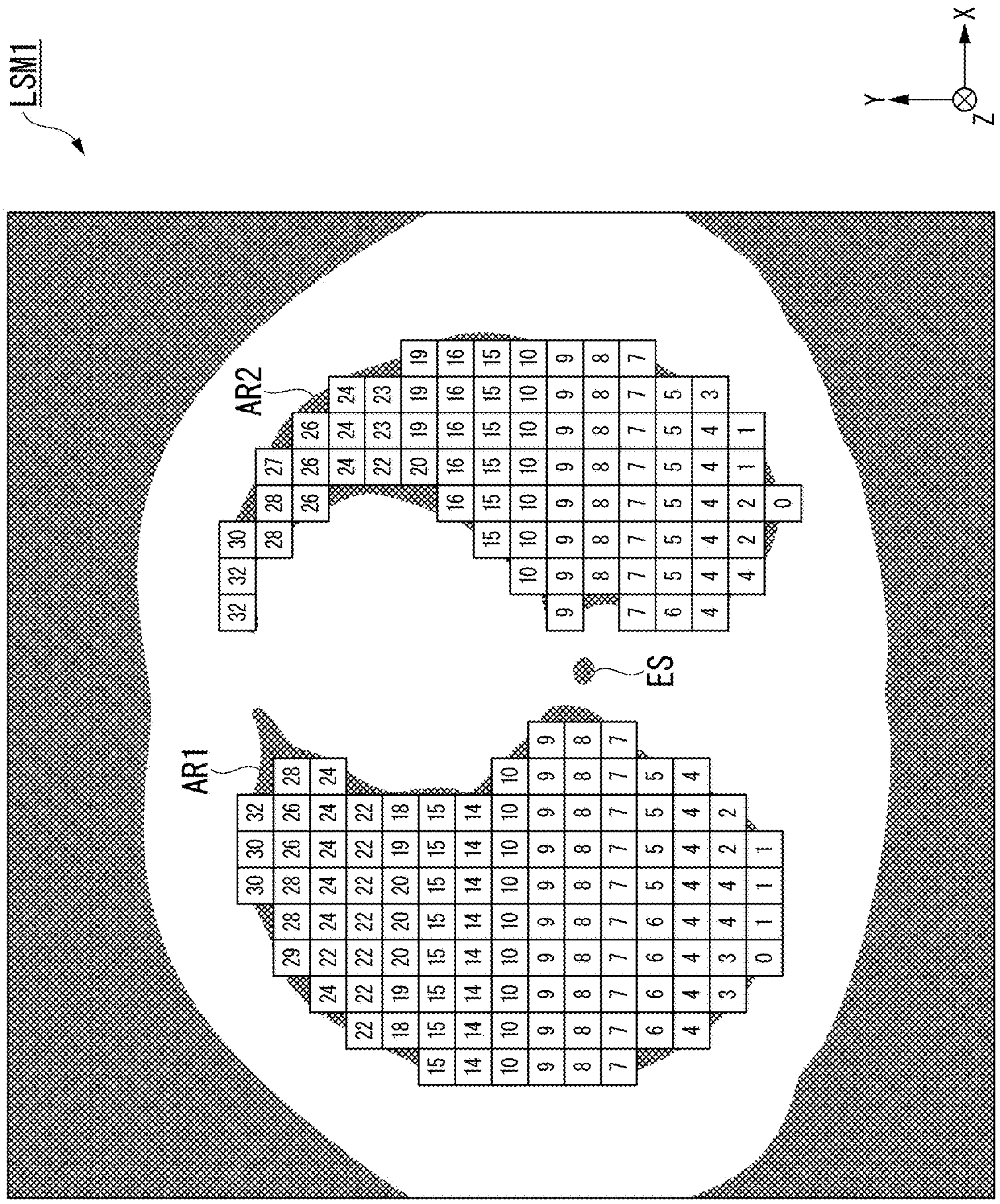
FIG. 5 is a diagram showing an example of a transpulmonary pressure map according to an embodiment.

FIG. 5 is a diagram showing an example of a transpulmonary pressure map LSM1 in which the numerical value of the transpulmonary pressure calculated for each unit region is superimposed on a CT image according to an embodiment. As shown in FIG. 5, a user such as a doctor can ascertain the detailed and accurate risk of lung injury of the patient P by checking such a transpulmonary pressure map LSM1.

Figure 6:
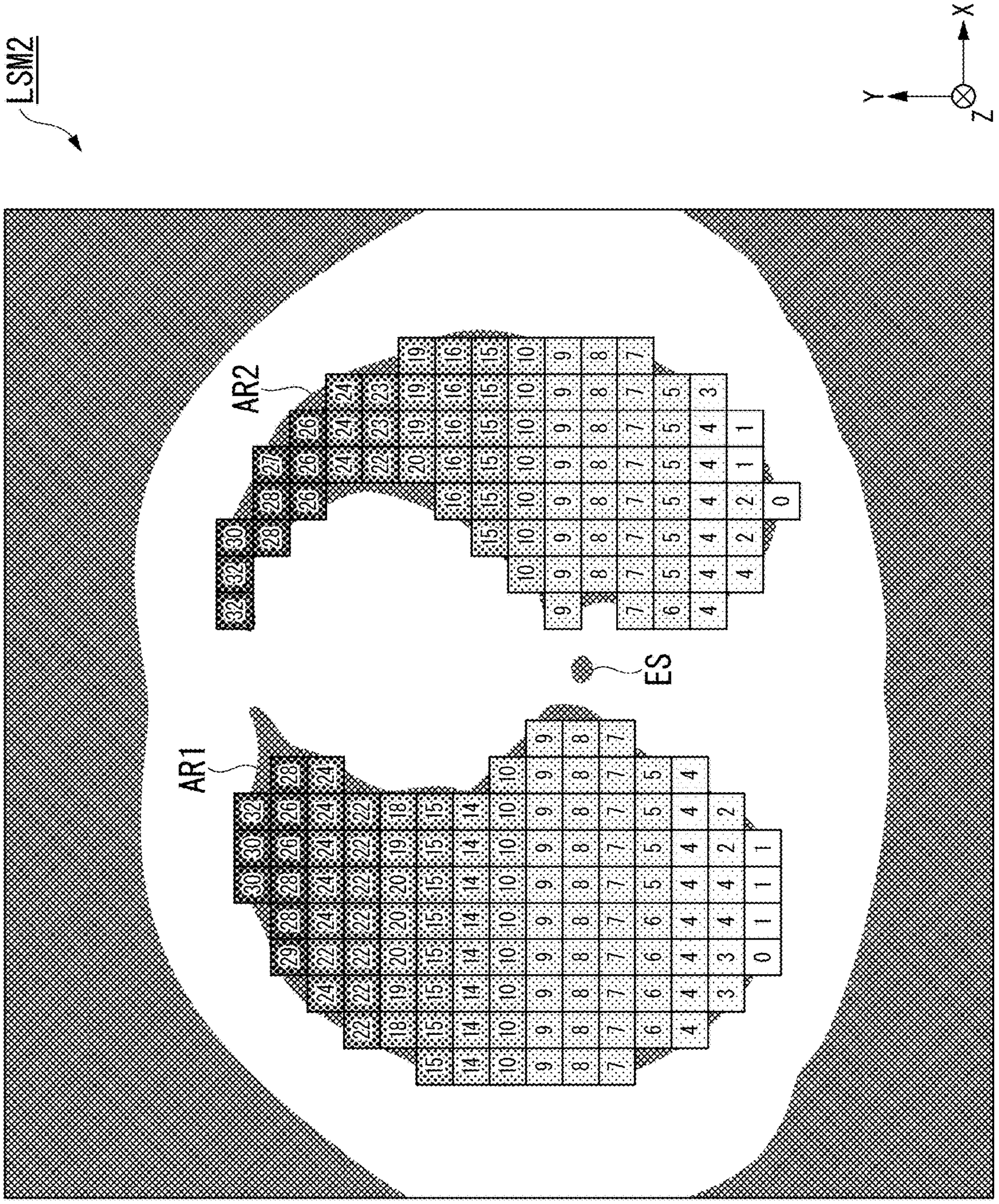
FIG. 6 is a diagram showing another example of a transpulmonary pressure map according to an embodiment.

Furthermore, by preparing in advance a lookup table in which transpulmonary pressure values are associated with display colors or grayscales, the generation function 144 can generate the transpulmonary pressure map as a color map image or grayscale image. The height distribution of transpulmonary pressures in the lung regions and degree thereof can be intuitively ascertained as colors or grayscales. FIG. 6 is a diagram showing an example of a transpulmonary pressure map LSM2 displayed as a grayscale image according to an embodiment. By checking the transpulmonary pressure map LSM2 displayed as such a grayscale image (or color image), a user such as a doctor can intuitively and easily ascertain the risk state of lung injury of the patient P.

Referring back to FIG. 2, subsequently, the estimation function 145 estimates risk information in the lung regions of the patient P on the basis of the transpulmonary pressure map (step S117). For example, the estimation function 145 estimates a high-risk region where the risk of lung injury is particularly high. The estimation function 145 estimates the risk information using, for example, a risk estimation model M pre-stored in the memory 150.

Figure 7A:
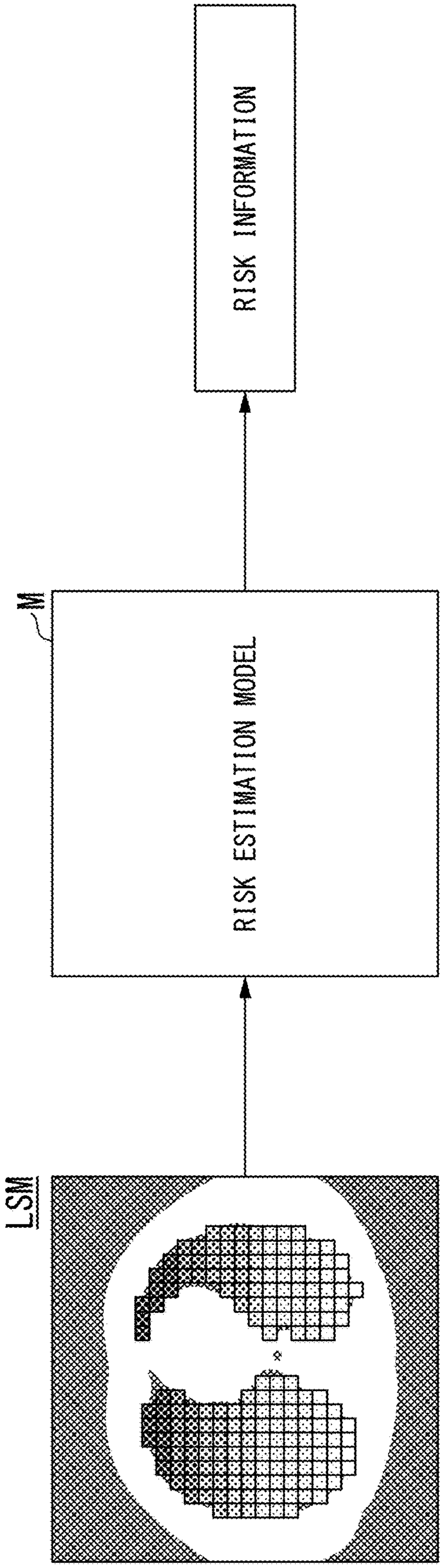
FIG. 7A is a diagram showing an example of input and output of a risk estimation model M according to an embodiment.
Figure 7B:
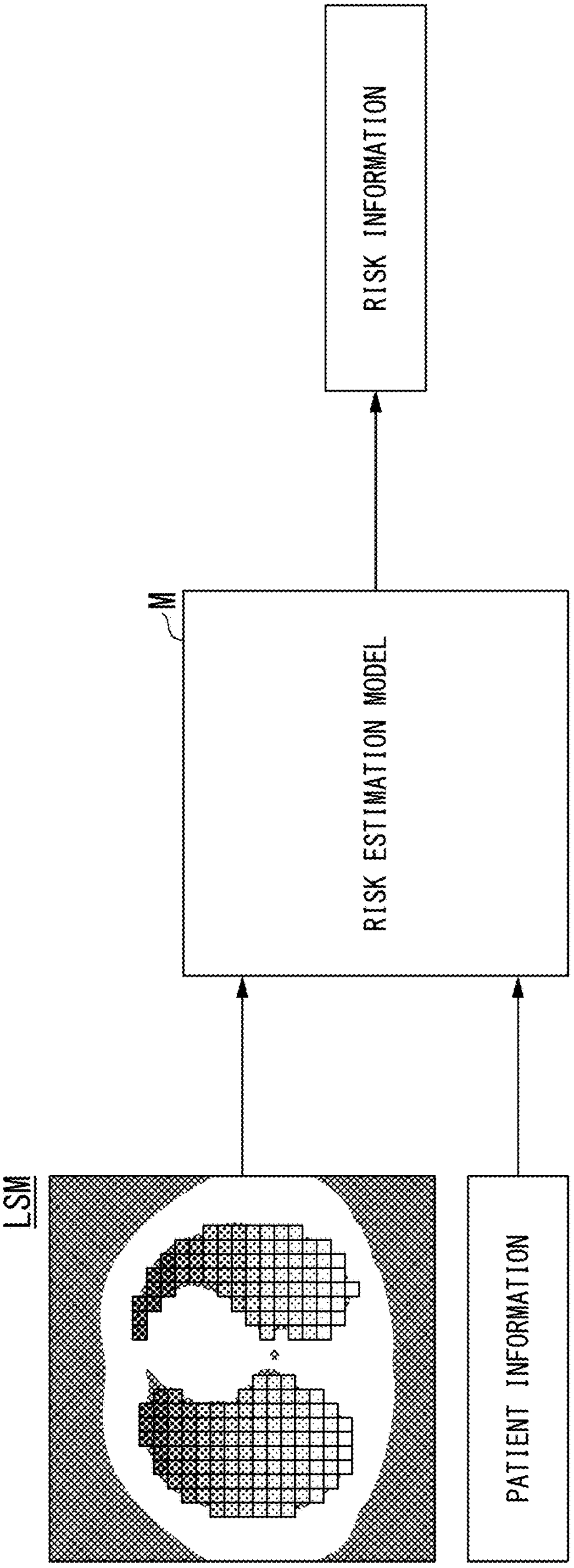
FIG. 7B is a diagram showing another example of input and output of the risk estimation model M according to an embodiment.

FIG. 7A and FIG. 7B are diagrams showing input and output of the risk estimation model M according to an embodiment. The risk estimation model M shown in FIG. 7A is a model trained to output risk information when a transpulmonary pressure map LSM (risk information map) or information based on the transpulmonary pressure map LSM (for example, numerical information on transpulmonary pressures, information on the proportion of the area of regions where transpulmonary pressures are equal to or greater than a threshold value to the area of the entire lung region, and the like) is input. The risk information includes, for example, information indicating a high-risk region and information indicating a prognosis prediction (a mortality rate, a treatment method, and the like). Further, the risk estimation model M shown in FIG. 7B is a model trained to output risk information when a transpulmonary pressure map LSM (risk information map) or information based on the transpulmonary pressure map LSM (e.g., numerical information on transpulmonary pressures and the like) and patient information are input. The patient information includes, for example, information included in a chart (a medical history, a smoking status, and the like), clinical information, and the like. In such a risk estimation model M, risk information can be estimated in detail by determining a distribution pattern of the transpulmonary pressures in addition to the proportion of the area of regions where transpulmonary pressures are equal to or greater than the threshold value to the entire area of the lung regions. Even if the proportion of the area of the regions where the transpulmonary pressures are equal to or greater than the threshold value to the entire area of the lung regions is the same, a treatment method can be changed by ascertaining the risk level according to the distribution pattern. For example, when the transpulmonary pressure on the ventral side is higher than that on the dorsal side, the risk can be reduced by changing the position of a patient to a prone position. Further, there is a recent method of monitoring the state of the lungs in real time during artificial respiration management using Electrical Impedance Tomography (EIT). The transpulmonary pressure map LSM is initial values of the state of the lungs, and EIT is the state of the lungs at time t during artificial respiration management. The transpulmonary pressure map LSM at time t may be estimated using a model that uses the transpulmonary pressure map LSM and EIT as inputs. In addition, the risk of developing ventilator-associated lung injury during artificial respiration management may be predicted using a model that uses the transpulmonary pressure map LSM and EIT as inputs.

Referring back to FIG. 2, subsequently, the display control function 146 causes the display 130 to display the generated transpulmonary pressure map LSM and the estimated risk information (step S119). By checking the transpulmonary pressure map LSM and the risk information, the user such as a doctor can perform detailed and accurate risk evaluation of lung injury of the patient P. Accordingly, processing of this flowchart ends.

Although an example of a case in which the transpulmonary pressure is calculated for each unit region PG (each pixel) has been described above, grids may be formed with a predetermined size at the time of display, and a transpulmonary pressure map may be generated and displayed using a representative value such as the average value of transpulmonary pressures within each grid. A region where a transpulmonary pressure is equal to or greater than the threshold value may be highlighted and displayed. A region where a transpulmonary pressure is equal to or greater than the predetermined threshold value may be regarded as a region where the risk of ventilator-associated lung injury is high or a region where the risk of ventilator-associated complications is high (e.g., pneumothorax, pneumomediastinum, pneumatocele, and the like), and the region may be highlighted and displayed. For example, a display method such as surrounding the region on a CT image with a contour or overlaying the region may be adopted.

Further, a lung region may be divided into a plurality of sections, and statistics of transpulmonary pressures may be calculated for each section, and the statistics may be displayed or displayed as a color map image or a grayscale image according to a lookup table. The method of dividing a lung region into a plurality of sections is, for example, to divide the lung region into four sections by dividing the lung region into two sections, the left lung and the right lung, in the horizontal direction and dividing the lung region into two sections, the ventral side and the dorsal side, in the vertical direction. As statistics, the average, median, maximum, minimum, variance, or the like can be used. Such a display makes it possible to visualize a distribution of the risk of ventilator-associated lung injury. Furthermore, a bias in the risk level, such as a left-right ratio or a top-bottom ratio, may be quantified or verbalized and displayed.

As the aforementioned method of dividing into sections, division may be performed on the basis of a CT value range of a CT image. For example, the method includes a method of dividing a lung region into hyperinflated lungs of −1,000 to −900 HU, normal lungs of −900 to −500 HU, poorly aerated lungs of −500 to −200, and atelectasis of −200 to +100. A distribution range (maximum to minimum or the like) and a distribution pattern of transpulmonary pressures or $h^*\{1-(H_{Avg}/-1000)\}$ may be displayed. Such a display allows the uniformity/non-uniformity of the air distribution in the lungs to be quantified and visualized. Further, an alert may also be issued to the user depending on the risk of ventilator-associated lung injury.

In addition, the transpulmonary pressure map LSM may be generated using values different from the airway pressure and esophageal pressure acquired in step S103. For example, if the transpulmonary pressure map LSM is generated using a value higher than the airway pressure acquired in step S103, a transpulmonary pressure map LSM can be obtained on the assumption that settings of the artificial ventilator are changed such that the airway pressure increases. By comparing with the transpulmonary pressure map LSM generated using the airway pressure acquired in step S103, it is possible to determine whether the settings of the artificial ventilator can be changed safely.

According to the medical information processing device 100 of the embodiment described above, it is possible to evaluate a lung injury risk in detail and accurately for the entire lungs in consideration of the lung condition of each individual patient. In addition, it is possible to perform artificial respiration management in accordance with the patient's condition, and it is possible to prevent worsening of lung injury by visualizing the risk early, and thus it is expected that the patient prognosis will improve.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing device comprising processing circuitry configured to:
- acquire a CT image of a chest of a subject;
- acquire an esophageal pressure and an airway pressure of the subject;
- calculate a local transpulmonary pressure for each unit region of an entire lung field of the subject in the CT image using a formula for calculating a transpulmonary pressure from CT values in a CT image, an esophageal pressure, and an airway pressure;
- generate a risk information map indicating the local transpulmonary pressure for each unit region;
- estimate risk information in the lung field of the subject using the local transpulmonary pressure for each unit region in the risk information map; and
- display the risk information map and the risk information on a display.

2. The medical information processing device according to claim 1, wherein the processing circuitry is further configured to superimpose the risk information map on the CT image and display the CT image including the risk information map on the display.

3. The medical information processing device according to claim 1, wherein the processing circuitry is further configured to estimate the risk information using a risk estimation model trained to output the risk information when the risk information map is input.

4. The medical information processing device according to claim 1, wherein the processing circuitry is further configured to estimate the risk information using a risk estimation model trained to output information indicating the risk information when the risk information map and information on the subject are input.

5. The medical information processing device according to claim 1, wherein the formula calculates the local transpulmonary pressure from the CT values in the CT image, the esophageal pressure, the airway pressure, and a relative positional relationship between a measurement position of the esophageal pressure in the CT image and the unit region for which the local transpulmonary pressure is to be calculated.

6. The medical information processing device according to claim 5, wherein the relative positional relationship indicates a height of the unit region for which the local transpulmonary pressure is to be calculated with reference to the measurement position of the esophageal pressure in a height direction orthogonal to a body axis direction of the subject in the CT image.

7. The medical information processing device of claim 5, wherein the processing circuitry is further configured to calculate, as the CT values in the formula, an average value of CT values of all pixels present in a region of interest from the unit region for which the local transpulmonary pressure is to be calculated to the measurement position of the esophageal pressure in a height direction orthogonal to a body axis direction of the subject in the CT image.

8. The medical information processing device of claim 1, wherein the processing circuitry is further configured to calculate a proportion of unit regions having transpulmonary pressures equal to or greater than a threshold value among the calculated transpulmonary pressure for each unit region, and display the proportion of the unit regions having transpulmonary pressures equal to or greater than the threshold value on the display.

9. The medical information processing device of claim 1, wherein the processing circuitry is further configured to generate a three-dimensional risk information map in a body axis direction of the subject using the CT images including a plurality of tomographic images of the chest captured in the body axis direction of the subject.

* * * * *